US008809596B2

(12) United States Patent
Maurer et al.

(10) Patent No.: US 8,809,596 B2
(45) Date of Patent: Aug. 19, 2014

(54) METHOD FOR PRODUCING DEODORIZED 1,2-PROPANEDIOL

(75) Inventors: Stephan Maurer, Neustadt-Gimmeldingen (DE); Roman Prochazka, Mannheim (DE); Oliver Bey, Niederkirchen (DE); Jochen Steiner, Bensheim (DE); Jochem Henkelmann, Mannheim (DE); Gerhard Theis, Maxdorf (DE); Peter Wahl, Heidelberg (DE); Frank Heimann, Ludwigshafen (DE)

(73) Assignee: BASF SE (DE)

( * ) Notice: Subject to any disclaimer, the term of this patent is extended or adjusted under 35 U.S.C. 154(b) by 266 days.

(21) Appl. No.: 13/145,722

(22) PCT Filed: Jan. 19, 2010

(86) PCT No.: PCT/EP2010/050597
§ 371 (c)(1),
(2), (4) Date: Jul. 21, 2011

(87) PCT Pub. No.: WO2010/084118
PCT Pub. Date: Jul. 29, 2010

(65) Prior Publication Data
US 2011/0282107 A1 Nov. 17, 2011

(30) Foreign Application Priority Data

Jan. 21, 2009 (EP) .................................... 09151011

(51) Int. Cl.
*C07C 31/18* (2006.01)
(52) U.S. Cl.
USPC ........... 568/868; 568/852; 568/858; 568/861; 568/913

(58) Field of Classification Search
None
See application file for complete search history.

(56) References Cited

U.S. PATENT DOCUMENTS

| 6,133,489 A | 10/2000 | Mohr et al. |
| 2010/0240934 A1 | 9/2010 | Henkelmann et al. |
| 2010/0312023 A1* | 12/2010 | Henkelmann et al. ........ 568/858 |
| 2010/0312024 A1 | 12/2010 | Henkelmann et al. |

FOREIGN PATENT DOCUMENTS

| DE | 524101 C | 5/1931 |
| DE | 4302464 A1 | 8/1994 |
| WO | WO-9727164 A1 | 7/1997 |
| WO | WO-2004041759 A1 | 5/2004 |
| WO | WO-2008020077 A1 | 2/2008 |

OTHER PUBLICATIONS

Dasari, M. A., et al., "Low-Pressure Hydrogenolysis of Glycerol to Propylene Glycol", Applied Catalysis A: General, vol. 281, (2005), pp. 225-231.
International Preliminary Report on Patentability for PCT/EP2010/050597 dated Jul. 26, 2011.
Translation of the International Preliminary Report on Patentability for PCT/EP2010/050597 dated Jul. 26, 2011.

* cited by examiner

*Primary Examiner* — Sudhakar Katakam
(74) *Attorney, Agent, or Firm* — Drinker Biddle & Reath LLP

(57) ABSTRACT

The present invention relates to a process for preparing deodorized 1,2-propanediol, to the use of the purified propanediol and to an apparatus for performing the process.

5 Claims, 1 Drawing Sheet

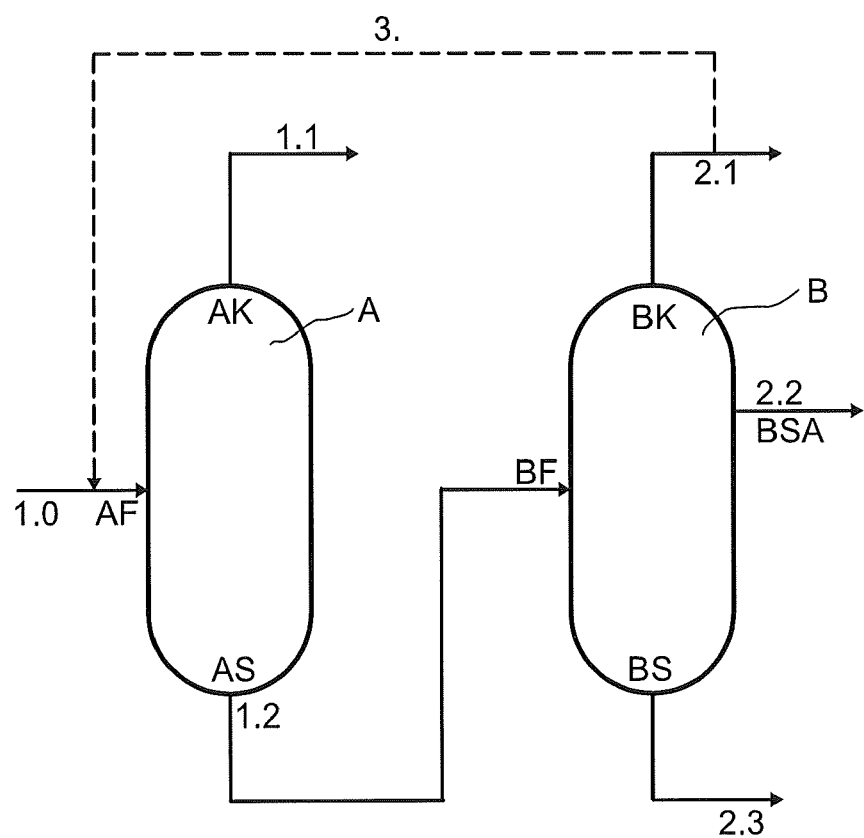

METHOD FOR PRODUCING DEODORIZED 1,2-PROPANEDIOL

CROSS-REFERENCE TO RELATED APPLICATIONS

This application is a national stage application (under 35 U.S.C. §371) of PCT/EP2010/050597, filed Jan. 19, 2010, which claims benefit of EP 09151011.5, filed Jan. 21, 2009.

BACKGROUND OF THE INVENTION

The present invention relates to a process for preparing deodorized 1,2-propanediol by distillative workup of the hydrogenation output obtained in the hydrogenation of glycerol.

Processes for preparing raw materials and especially fuels from biogenic fatty or oily starting mixtures and, for example, used oils and animal fats which occur in restaurants have been known for a long time, preference being given to using rapeseed oil as the starting material in the production of biogenic fuels. Biogenic oils and fats themselves are not very suitable as a motor fuel, since they have to be purified beforehand by usually complex processes. These include the removal of lecithins, carbohydrates and proteins, the removal of so-called oil sludge and the removal of the free fatty acids which are present, for example, in relatively large amounts in rapeseed oil. Vegetable oils processed in this way nevertheless deviate from the technical properties of conventional diesel fuels in several aspects. For instance, they generally have a higher density than diesel fuel, the cetane number of rapeseed oil is lower than that of diesel fuel, and the viscosity is several times higher than that of diesel fuels. One known way of solving the associated problems is to convert the triglycerides present in the biogenic oil and fat starting mixtures to fatty acid monoalkyl esters, especially methyl or ethyl esters. These esters, also referred to as "biodiesel", can generally be used in diesel engines without major modifications. The transesterification of the triglycerides for biodiesel production also produces glycerol, from which 1,2-propanediol can be obtained in a manner known per se by hydrogenation.

For instance, DE-C 524 101 describes such a process, in which glycerol, among other materials, is subjected to a gas phase hydrogenation in the presence of a hydrogenation catalyst with hydrogen in a considerable excess, using bromine-activated copper or cobalt catalysts. DE 4302464 A1 describes a process for preparing 1,2-propanediol by hydrogenating glycerol in the presence of a heterogeneous catalyst, wherein glycerol is passed over a catalyst bed of copper catalyst. PCT/EP2007/0511983 describes a process for preparing 1,2-propanediol, in which a glycerol-containing stream is subjected to a hydrogenation in the presence of a heterogeneous copper catalyst.

The glycerol-containing streams used here may also comprise numerous undesired components, such as sulfuric acid, hydrogen sulfide, thioalcohols, thioethers, carbon oxide sulfide and, for example, nitrogen compounds, e.g. amino acids. Even though the removal of these impurities actually before the hydrogenation of the glycerol is known, some of them are still present in the 1,2-propanediol after the hydrogenation of the glycerol. Such impurities can lead to the 1,2-propanediol obtained being unsuitable for particular applications owing to the odor emanating from them. More particularly, troublesome impurities are thiols, fatty acids, esters, aldehydes and ketones, some of which, being odor-intensive substances, can be perceived even in the ppb range.

BRIEF SUMMARY OF THE INVENTION

It is an object of the invention to provide a process for preparing deodorized 1,2-propanediol, which is suitable especially for workup of propanediol which is obtained through hydrogenation of glycerol which in turn originates from natural raw materials, especially rapeseed oil.

A process has now been found for purifying 1,2-propanediol to remove impurities by distillation, wherein the contaminated propanediol 1. is first conducted into a low boiler column A which comprises a rectifying section and a stripping section,
1.1 the low boilers, especially methanol, 1-propanol, 2-propanol, water and low-boiling odorous substances, being removed via the top of the column and
1.2 a 1,2-propanediol stream which still comprises impurities being drawn off via the bottom of the column, and being
2. introduced into a column B for purifying distillation,
2.1 purified, low-odor 1,2-propanediol leaving the column as a liquid side draw,
2.2 a preferably minor stream of still-contaminated odor-containing 1,2-propanediol being drawn off via the top of column B and
2.3 high boilers such as ethylene glycol and glycerol being removed via the bottom.

BRIEF DESCRIPTION OF THE FIGURES

FIG. 1 shows the schematic structure of a column arrangement which is advantageous for the process according to the invention.

DETAILED DESCRIPTION OF THE INVENTION

In a preferred embodiment, the still-contaminated 1,2-propanediol is conducted into a low boiler column A which is provided with internals known to those skilled in the art. This column comprises, in the rectifying section, preferably fewer than 20 theoretical plates, typically fewer than 5 theoretical plates. The stripping section comprises preferably fewer than 40 theoretical plates, typically fewer than 15 theoretical plates. The reflux ratio is preferably less than 5, more preferably less than 1. The bottom temperature of the low boiler column A is preferably less than 200° C., more preferably less than 180° C. Via the top of the low boiler column A, it is preferably possible to remove low boilers such as methanol, 1-propanol, 2-propanol and water, and also low-boiling odorous substances. The 1,2-propanediol stream which still contains odorous substances and has been drawn off via the bottom of the column may still comprise high-boiling components such as ethylene glycol and glycerol.

In the column for purifying distillation B, ethylene glycol and glycerol in particular are removed essentially via the bottom. The purified low-odor 1,2-propanediol product stream leaves the column as a liquid side draw with a preferably relatively low ethylene glycol concentration of especially less than 2000 ppm by weight, more preferably less than 500 ppm by weight. Via the top of the column, it is possible to draw off a preferably minor stream of 1,2-propanediol still containing odorous substances with a possibly low ethylene glycol concentration, which, for odor discharge, can be recycled fully or partly back to the low boiler column A.

In a preferred embodiment, the still-contaminated propanediol drawn off from column A is a mixture which consists of at least 90% and preferably 97% by weight of 1,2-propanediol, based on the total weight. The purified propanediol drawn off from column B preferably has a concentration of at least 99%, preferably 99.5% and especially 99.7% by weight of propanediol with a maximum proportion of odor-intensive substances of 0.01% and especially 0.001% by weight and a maximum proportion of ethylene glycol of 0.2% and preferably 0.05% by weight. Odor-intensive substances are understood here to mean especially thiols, fatty acids, esters, aldehydes and ketones.

In this preferred embodiment, there are fewer than 60 theoretical plates in the rectifying section of column B above the liquid side draw, more preferably fewer than 40 theoretical plates. There are preferably fewer than 120 theoretical plates between the feed point and the liquid side draw, more preferably fewer than 80 theoretical plates. The stripping section comprises preferably fewer than 60 theoretical plates, especially fewer than 40 theoretical plates. The reflux ratio at the top of column B, based on the feed of the purifying distillation column B, is preferably less than 10, more preferably less than 6. The bottom temperature of column B is preferably less than 200° C., more preferably less than 180° C.

The 1,2-propanediol to be purified originates, in a preferred embodiment, from the hydrogenation output obtained in the hydrogenation of glycerol to 1,2-propanediol using preferably copper catalysts, the glycerol being obtained especially from renewable raw materials such as rapeseed oil.

The invention further relates to an apparatus for performing the process according to the invention. FIG. 1 shows the schematic structure of a column arrangement which is advantageous for the process according to the invention. Contaminated propanediol is supplied via a feed line 1.0 into the low boiler column A which has a column top AK and a column bottom AS. The low boilers can be drawn off from column top AK via line 1.1; the still-contaminated propanediol is drawn off from the column bottom AS via the outlet 1.2 and introduced into column B via the feed BF. Column B has a column top BK, from which still-contaminated propanediol is drawn off via line 2.1, which can be passed back into the contaminated propanediol stream 1.0 via line 3.

The high boilers can be drawn off from the column bottom BS via line 2.3; the purified propanediol leaves column B via the side draw BSA (line 2.2.).

Distillation columns A and B may entirely or partly comprise packings composed of ordered or unordered separating elements, at which the vapor ascending between bottom and top, and the liquid flowing downward are brought into intimate contact. The separating internals used may, as well as random packings, for example composed of Raschig rings, Pall rings, ceramic saddles, also be structured packings. These may be manufactured, for example, from perforated metal sheets, from metal fabrics or else from plastic or ceramic material. The distillation columns may also have trays, for example sieve trays, bubble-cap trays, valve trays and tunnel-cap trays. Particularly preferred trays are Thormann trays.

In a particularly preferred embodiment, the distillation column A has, in the rectifying section, trays, especially Thormann trays, and, in the stripping section, a structured packing. In a further preferred embodiment, column B is entirely a packed column with a random packing or a structured packing.

The outer dimensions of the distillation columns are variable depending on the built-in components; when implemented in industry, the distillation columns in a preferred embodiment have the following dimensions:

distillation column A: diameter 1 to 3 m, height 10 to 30 m
distillation column B: diameter 3.5 to 5 m, height 40 to 80 m.

However, dimensions outside these ranges are also possible.

In one embodiment of the invention, especially in column B, but if appropriate also in column A, it is possible to use distillation aids, especially azeotroping agents, in order to improve the distillative removal of the impurities from 1,2-propanediol. Suitable aids are, for example, benzene, toluene and xylene. These aids can be used, for example, in an amount of preferably less than 10%, especially less than 1% and more preferably in the ppm range, based on the material to be distilled in at least one of the two columns, especially in column B.

In a further preferred embodiment of the invention, the process according to the invention is performed in at least one of the two columns A and B in the presence of a reducing phosphorus compound, in a manner known per se from WO 97/27164 A 1. This can be done by a surface treatment of the inner surfaces of the plant parts, and continuously or batchwise. In batchwise mode, the plants can be treated completely or partially with the phosphorus compound before the distillation. In continuous mode, the phosphorus compound can be added to the product stream. This achieves a significant reduction in the aldehyde content. Preferred phosphorus compounds may be inorganic or organic phosphorus compounds or a combination thereof. In a preferred embodiment, the phosphorus compound is one with trivalent phosphorus.

Preference is given to phosphorous acid (which is present predominantly in the stable tautomeric form $HP(O)(OH)_2$) and salts thereof. Salts of phosphorous acid are preferably selected from water-soluble salts, such as especially alkali metal, zinc and calcium phosphites. Particularly preferred alkali metal phosphites are sodium and potassium phosphite. The corresponding hydrogenphosphites are likewise usable. Most preferred, however, is the use of the acid itself.

When the phosphorus compound is added to the mixture itself, this is usually carried out in such a way that the phosphorus compound is present in a proportion of about 10 to about 5000 ppm before glycol is removed from the mixture. The proportion should preferably be in the range from about 100 to about 1000 ppm, and especially about 500 ppm.

The propanediol purified in accordance with the invention, owing to its lack of odor, is suitable in principle for all purposes in which 1,2-propanediol is used, especially fountain solutions, adhesives, cooling fluids and especially foods, pharmaceuticals and cosmetics.

Example

The distillation of contaminated propanediol was performed in a column arrangement according to FIG. 1. The low boiler column A used was a laboratory column with an internal diameter of 50 mm in the rectifying section and 43 mm in the stripping section. The internals used were 10 bubble-cap trays to achieve the separating task in the aqueous rectifying section, and a Montz A3 750 structured packing in the stripping section. The packing height in the stripping section was 0.64 m.

The heating of the column at the bottom was effected with a thin-layer evaporator, and the top condensation by means of cooling water. The offgas (temperature approx. 25° C. at the top condenser) was conducted through cold traps cooled with dry ice. The column was trace-heated and was operated at a bottom temperature of 153° C. and a top pressure of 300 mbar abs.

The purifying distillation was performed in a column B which has an internal diameter of 64 mm. The feed was added at a packing height of 1.64 m, calculated from the bottom. At packing height 4.55 m, the pure 1,2-propanediol product was withdrawn as a liquid side stream. The total packing height was 5.85 m of Montz A3 750.

The heating of the column at the bottom was effected with a metallic falling-film evaporator, the top condensation with cooling water. The offgas (temperature approx. 25° C. ex top condenser) was conducted through dry ice-cooled traps. The column was trace-heated and was operated at a bottom temperature of 153° C. and a top pressure of 200 mbar abs. The following results were obtained:

|  | Unit | Low boiler column A | Column for purifying distillation B |
| --- | --- | --- | --- |
| Top pressure | mbar abs. | 300 | 200 |
| Bottom temperature | ° C. | 153 | 153 |
| Reflux ratio | kg/kg | 0.8 | — |
| Reflux to feed rate | kg/kg | — | 3.9 |
| F factor | Pa$^{0.5}$ | 0.4-0.9 | 0.5 |

| Concentrations: | Unit | feed AF | top AK | bottom AS | top BF | bottom BS | side draw BSA |
| --- | --- | --- | --- | --- | --- | --- | --- |
| water | % by wt. | 25.40 | 95.60 | 0.02 | 0.27 | 0.02 | 0.03 |
| methanol | % by wt. | 0.40 | 1.50 | <0.005 | <0.005 | <0.005 | <0.005 |
| 2-propanol | % by wt. | 0.20 | 0.50 | <0.005 | <0.005 | <0.005 | <0.005 |
| 1-propanol | % by wt. | 0.70 | 2.70 | <0.005 | <0.005 | <0.005 | <0.005 |
| 1,2-propanediol | % by wt. | 72.10 | 0.02 | 98.70 | 99.60 | 13.00 | 99.90 |
| ethylene glycol | % by wt. | 0.80 | <0.01 | 1.00 | <0.01 | 52.90 | 0.046 |
| glycerol | % by wt. | 0.50 | <0.02 | 0.60 | <0.02 | 31.50 | <0.02 |

The invention claimed is:

1. A process for purifying 1,2-propanediol to remove impurities by distillation, comprising:
   1. conducting contaminated propanediol into a low boiler column A which comprises a rectifying section and a stripping section, said low boiler column A having less than 20 theoretical plates in the rectifying section and less than 40 theoretical plates in the stripping section, and has a reflux ratio of less than 5 and wherein the bottom temperature of column A is less than 200° C.,
   1.1 removing low boilers via the top of the column and
   1.2 drawing off a 1,2-propanediol stream which still comprises impurities via the bottom of the column, wherein the 1,2-propanediol stream comprises at least 97% by weight 1,2-propanediol, and
   2. introducing the 1,2-propanediol stream into a column B for purifying distillation,
   2.1 removing purified, low-odor 1,2-propanediol from column B as a liquid side draw,
   2.2 drawing off a stream of still-contaminated, odor-containing 1,2-propanediol via the top of column B and
   2.3 removing high boilers via the bottom of column B.

2. The process of claim 1, wherein, the purifying distillation column B comprises a rectifying section, a feed point, a liquid side draw, and a stripping section, wherein there are less than 60 theoretical plates in the rectifying section above the liquid side draw, less than 120 theoretical plates between the feed point and the liquid side draw, and less than 60 theoretical plates in the stripping section, and wherein column B has a reflux ratio at the top of column B, based on the feed of the purifying distillation column, of less than 10, and wherein the bottom temperature of column B is less than 200° C.

3. The process of claim 1, wherein the contaminated propanediol introduced into column A is contaminated with thiols, fatty acids, esters, aldehydes and/or ketones.

4. The process of claim 1, wherein the purified propanediol, after removal from the purifying distillation column B, comprises at least 99% by weight of pure 1,2-propanediol and not more than 0.01% by weight of thiols, fatty acids, esters, aldehydes and/or ketones, and not more than 0.1% by weight of ethylene glycol.

5. The process of claim 1, wherein the contaminated propanediol is obtained by hydrogenating a glycerol-containing stream in the presence of a catalyst.

* * * * *